(12) United States Patent
Wallenstein et al.

(10) Patent No.: US 8,403,969 B2
(45) Date of Patent: Mar. 26, 2013

(54) ANTERIOR VERTEBRAL PLATE WITH QUICK LOCK SCREW

(75) Inventors: Todd M. Wallenstein, Ashburn, VA (US); Peter M. Harris, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 1014 days.

(21) Appl. No.: 11/700,232

(22) Filed: Jan. 31, 2007

(65) Prior Publication Data

US 2008/0234748 A1    Sep. 25, 2008

(51) Int. Cl.
*A61B 17/70* (2006.01)
*A61B 17/58* (2006.01)
*A61B 17/56* (2006.01)

(52) U.S. Cl. ...................................... 606/289

(58) Field of Classification Search ............ 606/69, 606/70, 71, 60, 246–279, 280–299, 300–331; 411/378–426
See application file for complete search history.

(56) References Cited

U.S. PATENT DOCUMENTS

| | | | |
|---|---|---|---|
| 5,954,722 A * | 9/1999 | Bono | 606/281 |
| 6,030,389 A * | 2/2000 | Wagner et al. | 606/71 |
| 6,193,721 B1 * | 2/2001 | Michelson | 606/70 |
| 6,224,602 B1 * | 5/2001 | Hayes | 606/296 |
| 6,322,562 B1 * | 11/2001 | Wolter | 606/62 |
| 6,669,700 B1 * | 12/2003 | Farris et al. | 606/287 |
| 6,730,091 B1 * | 5/2004 | Pfefferle et al. | 606/70 |
| 7,063,701 B2 * | 6/2006 | Michelson | 606/307 |
| 7,220,263 B2 * | 5/2007 | Cordaro | 606/70 |
| 7,318,825 B2 * | 1/2008 | Butler et al. | 606/71 |
| 7,322,983 B2 * | 1/2008 | Harris | 606/273 |
| 7,322,984 B2 * | 1/2008 | Doubler et al. | 606/70 |
| 7,766,948 B1 * | 8/2010 | Leung | 606/305 |
| 2003/0153919 A1 * | 8/2003 | Harris | 606/69 |
| 2003/0187442 A1 * | 10/2003 | Richelsoph et al. | 606/70 |
| 2005/0149026 A1 * | 7/2005 | Butler et al. | 606/69 |
| 2005/0192578 A1 * | 9/2005 | Horst | 606/69 |
| 2006/0235400 A1 * | 10/2006 | Schneider | 606/69 |
| 2006/0276793 A1 * | 12/2006 | Berry | 606/69 |

* cited by examiner

*Primary Examiner* — Kevin T Truong
*Assistant Examiner* — Christopher Beccia
(74) *Attorney, Agent, or Firm* — Carter, DeLuca, Farrell & Schmidt, LLP

(57) ABSTRACT

Provided is a novel system that includes a low profile anterior vertebral body plate and quick lock screws for the fixation and stabilization of the cervical spine, the quick lock screw having an integral novel screw locking mechanism of a locking thread disposed on at least a portion of the side of the screw head, which engages an inwardly directed screw hole flange and thus attaches to the plate so as to lock the screw into the plate Also provided is a method of stabilizing cervical vertebrae using the disclosed system.

13 Claims, 6 Drawing Sheets

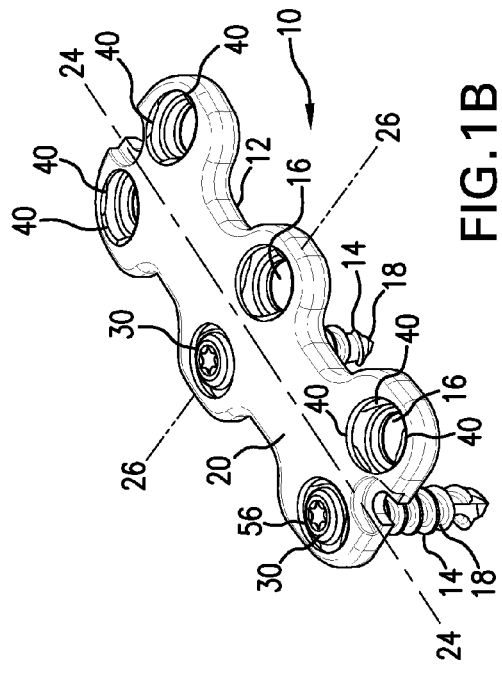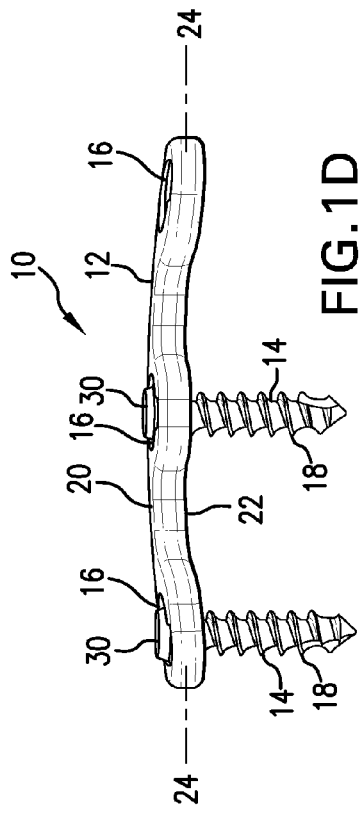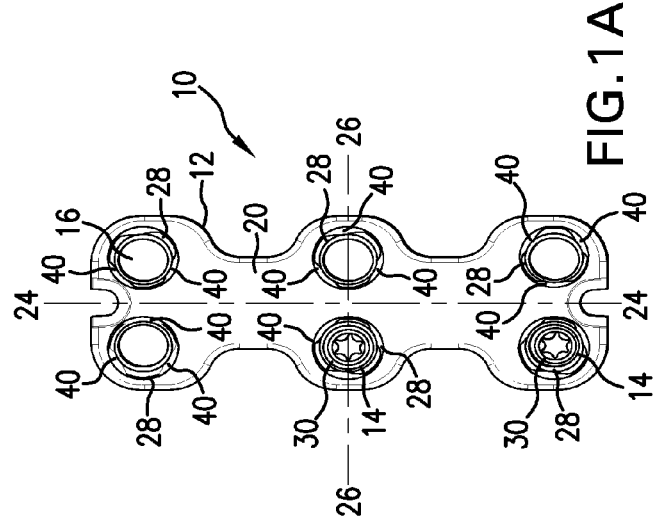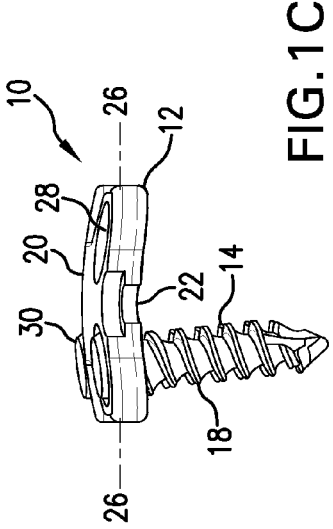

SECTION A-A

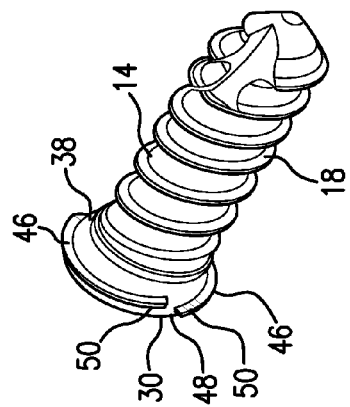
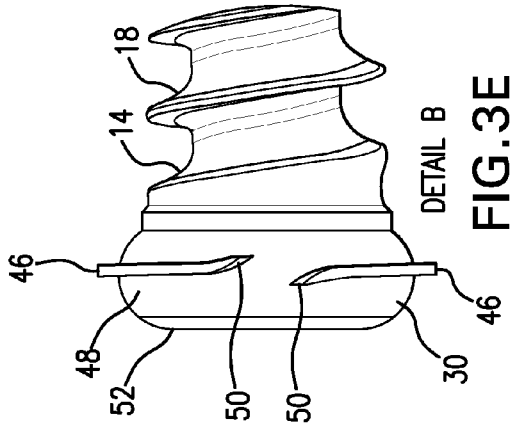
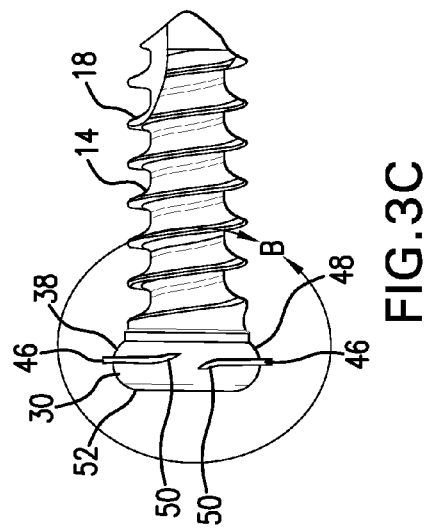
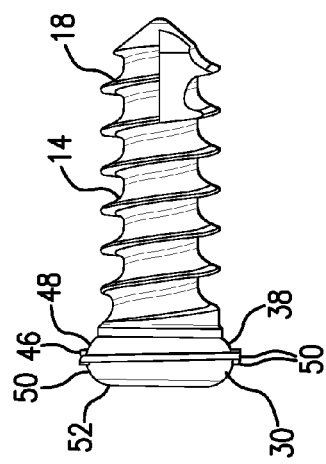
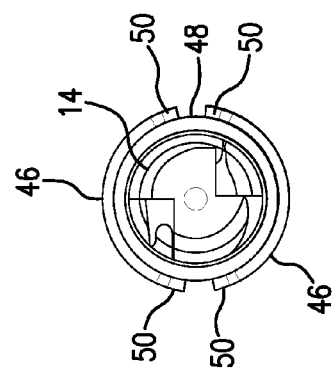

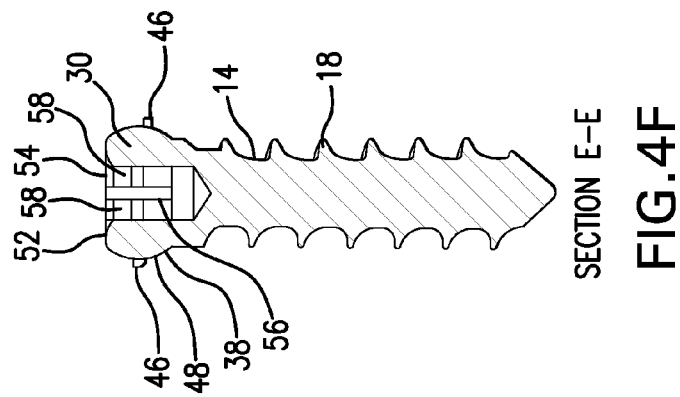
SECTION E-E FIG.4F
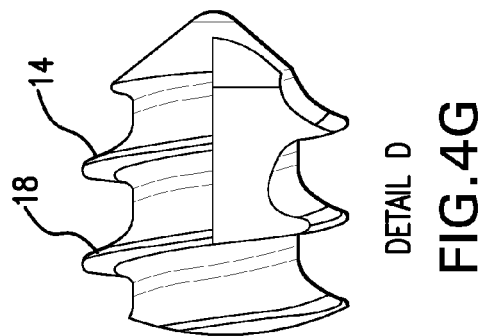
DETAIL D FIG.4G
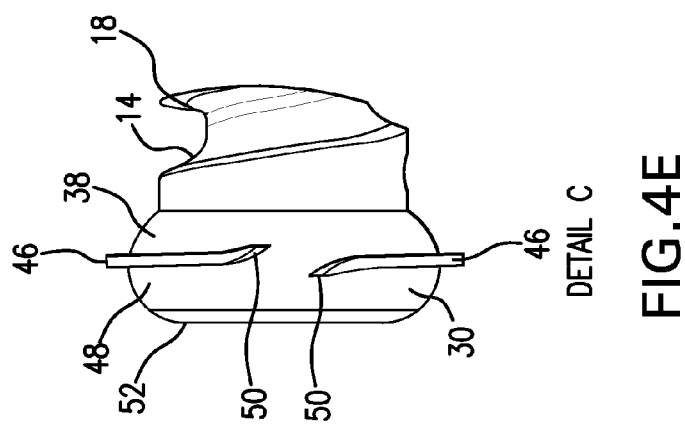
DETAIL C FIG.4E

ANTERIOR VERTEBRAL PLATE WITH QUICK LOCK SCREW

BACKGROUND OF THE INVENTION

1. Technical Field

The present invention relates to devices and methods for use in orthopedic spine surgery. In particular, the present invention relates to a system that provides a low profile anterior vertebral body plate and quick lock screws for the fixation and stabilization of the cervical spine, the quick lock screw in combination with the anterior vertebral plate providing a novel screw locking mechanism that requires no additional locking elements.

2. Background Art

Disease, the effects of aging, or physical trauma resulting in damage to the spine has been treated in many instances by fixation or stabilization of the effected vertebra. The use of plates and screws for fixation and stabilization of the cervical vertebra has been widely accepted as a reliable practice and has proven to be highly successful clinically.

The various plates, which are attached to the anterior vertebral bodies of the spinal column by bone screws have some common features such as relatively planar body profiles that define multiple holes or slots through which the screws fit and are threaded into the bone. Various means have been used to prevent the screws from becoming loose or detached from their necessary secured or locked attachment to the vertebral plate. Among the differences between the conventionally used plates and screws is the manner in which the screws are locked into place in the hole or slot of the plate after the screws have been secured to the bone.

These conventional devices can be generally grouped into three basic categories with regard to how the screws are captured or secured in the plates.

Early plate designs were standard bone plates having holes through which screws were passed and screwed into the bone. These plates had no special provision for attaching the screws to the plate and as such were susceptible to having the screws back out of the plate over time. There have been clinically reported instances of screws backing out of these type plates with resulting surgical complications. Due to the potential and actual unreliable performance of such plates, the need for secure fixation of the screw to the plate as well as to the bone is now considered a basic requirement for vertebral plates. Due to the lack of predictable security of the screw to the plate, plates which do not secure the screw relative to the plate have fallen out of favor and virtually disappeared from use.

Efforts have been made to secure the screws relative to the plates. In one design the screw head contains a threaded hole configured to receive a set screw. After the screw has been driven into bone and the head is seated in the plate hole, the set screw is inserted into the receiving hole of the screw head. The set screw is tapered to cause the screw head to expand and frictionally engage the wall of the plate hole, thereby resisting forces which tend to cause the screw to back out. While such mechanisms have worked to some degree, the addition of a small additional part, the set screw, at the time of surgery presents the potential hazard of dropping the set screw into the surgical field or otherwise misapplying the set screw to the screw head, for example, cross threading.

An alternative approach has been to provide features in the plate, which are specifically designed to hold the screw in position once the screw is inserted through the plate and screwed into the bone. One direction taken in this effort has been to design plates that incorporate or attach individual retaining rings or snap features associated with each plate hole configured to hold the inserted screw in place relative to the plate. These plates are very common and widely used; however, an inherent problem associated with such plates is the use of the additional very small retaining elements that can become disengaged from the plate and migrate into the surrounding soft tissues. Further, difficulty experienced in accessing and disengaging the small locking elements and removing the screws from this type of plate has caused some concern for the continued use of such plates. A similar approach involves individual cams associated with each plate hole, which when rotated apply friction pressure to the screw head in an attempt to resist back out.

Another approach is to add a cover to the plate after the screws have been placed. Such a design undesirably adds steps to the surgical procedure, thickness or height to the overall construct, and is susceptible to misapplication. Yet another direction taken in this effort to provide plates with locking elements is to provide dedicated overlying features, which are attached to the top side of the vertebral plate for the purpose of covering at least a portion of the screw head and thereby holding the screw in a seated and locked position. Generally these plates are designed to provide a variety of screw covering features that are pre-attached to the plate, and which can be selectively slid or rotated into position once it has been inserted. In some devices, such covering plates cover multiple screw heads. These plates typically require an increase in the overall composite thickness of the plate in order to accommodate the additional locking feature attached to the top side of the plate. This is a particularly unacceptable condition due to the use of such plates in an area of the spine where a thin, smooth surfaced profile for the plate assembly is preferred. Another major problem with such plates is that the overlying locking element cannot always be properly positioned over the screw head if the screw shaft was, due to anatomical necessity, positioned through the plate and into the bone at an angle such that the screw head does not fully seat in the plate recess provided on the top side of the plate. Further, when one of the overlying locking elements of such a plate loosens or becomes disengaged it is then free to float away from the top side of the plate and migrate into the soft tissue adjacent to the top side of the vertebral plate.

Yet another approach is to provide machine threads in the plate hole with corresponding threads on the screw head. Thus the screw has a first, bone engaging thread on its shaft and a second machine thread on the screw head. As the thread shaft is screwed into bone the screw head approaches the plate hole and the machine thread engages the thread in the hole. Aside from the fact that there is nothing to prevent the same forces that urge the screw to back out of bone to have the same effect on the machine thread engagement, such an arrangement does not provide adequate clinical flexibility. First there is no assurance that the lead in thread of the machine thread will match up with the plate hole thread when the screw head reaches the hole, raising the possibility of cross threading. Second, the machine thread in the plate hole does not allow various angular positions between the screw and the plate, as the threads must match up and engage when the screw head reaches the hole. As to the latter point, one plate provides a threaded ring in the plate hole, which is intended to allow the head to assume a variety of angular positions.

There is therefore, an unfulfilled need for an anterior cervical plate system that can maintain a relatively low profile, as found in the non-locking plates while providing the security of a locking plate system. Further there is a need for a vertebral plate that does not have additional separate locking elements with the predictable problems of locking elements becoming disengaged from the plate and migrating away from the top side of the plate into the surrounding soft tissue.

SUMMARY OF THE DISCLOSURE

The present invention meets the above identified need by providing a low profile anterior vertebral body plate, which is secured to the underlying bone using novel quick lock screws.

Also provided is a low profile anterior vertebral body plate, which is secured to the underlying bone using novel quick lock screws having at least one integrally formed locking element that engages a corresponding lock receiving structure integrally formed in the plate so as to secure and lock the screw into a set position relative to the plate.

Also provided is a low profile anterior vertebral body plate, which is secured to the underlying bone using novel quick lock screws, each of the screws having a screw head with at least one integral locking thread circumferentially disposed around at least a portion of the side of the screw head, the locking thread being configured to engage a complimentary locking flange, which is inwardly directed from the upper portion of at least one section of the inside wall of the plate screw hole.

Also provided is a low profile anterior vertebral body plate, which is secured to the underlying bone using novel quick lock screws, each of the screws having a screw head with multiple independent locking threads disposed around the circumference of the side of the screw head, the locking threads being configured to respectively engage corresponding locking flanges, which are inwardly directed from the upper portion of the inside wall of the plate screw hole, the locking threads terminating at each end with a flange engagement edge.

Also provided is a low profile anterior vertebral body plate, which is secured to the underlying bone using novel quick lock screws, each of the screws having a screw head with at least one substantially flat pitch integral locking thread disposed around less than the full circumference of the side of the screw head, each of the at least one locking thread being configured to engage a complimentary locking flange, which is inwardly directed from the upper portion of at least one section of the inside wall of the plate screw hole.

Also provided is a novel bone screw capable of locking to an anterior vertebral body plate, the screw having a screw head with at least one substantially flat pitch locking thread disposed around less than the full circumference of the side of the screw head, the locking threads being configured to be capable of engaging a complimentary shaped locking flange disposed on the inner wall of a bone plate screw hole.

Also provided is a novel bone screw capable of locking to an anterior vertebral body plate, the screw having a screw head with multiple substantially flat pitch locking threads disposed around less than the full circumference of the side of the screw head, the screw head further having at least one loosening/removing tool engaging structure defined in the surface of the screw head.

Also provided is a novel low profile anterior vertebral body plate system including a plate and quick lock screws, the interaction between the quick lock screws and plate providing a locking mechanism not requiring any additional locking elements.

Also provided is a method of stabilizing spinal vertebrae, the method including providing a low profile anterior vertebral body plate, which is securely attached to the underlying bone of adjacent vertebrae using novel quick lock screws so as to hold one attached vertebra in a fixed position relative to the adjacent attached vertebra.

Also provided is a kit, which includes at least one low profile anterior vertebral body plate and a corresponding set of novel quick lock screws, the kit not requiring any additional locking elements.

BRIEF DESCRIPTION OF THE DRAWINGS

The foregoing and other features of the novel low profile anterior vertebral plate system will become apparent to one skilled in the art to which the disclosed system and devices relate upon consideration of the following description of exemplary embodiments with reference to the accompanying drawings, wherein:

FIGS. 1A-E respectively show top, isometric, end, side, and enlarged cross-sectional views of the low profile anterior vertebral plate with two quick lock bone screws fully seated in the respective screw holes.

FIGS. 3A-E respectively show side, isometric, alternate side, threaded end, and screw head detail views of the quick lock screw.

FIGS. 4A-G respectively show side, isometric, alternative side, threaded end, screw head detail view, side cross-sectional view and threaded end detail views of the quick lock screw.

DETAILED DESCRIPTION OF PREFERRED EMBODIMENTS

Figure 1E:
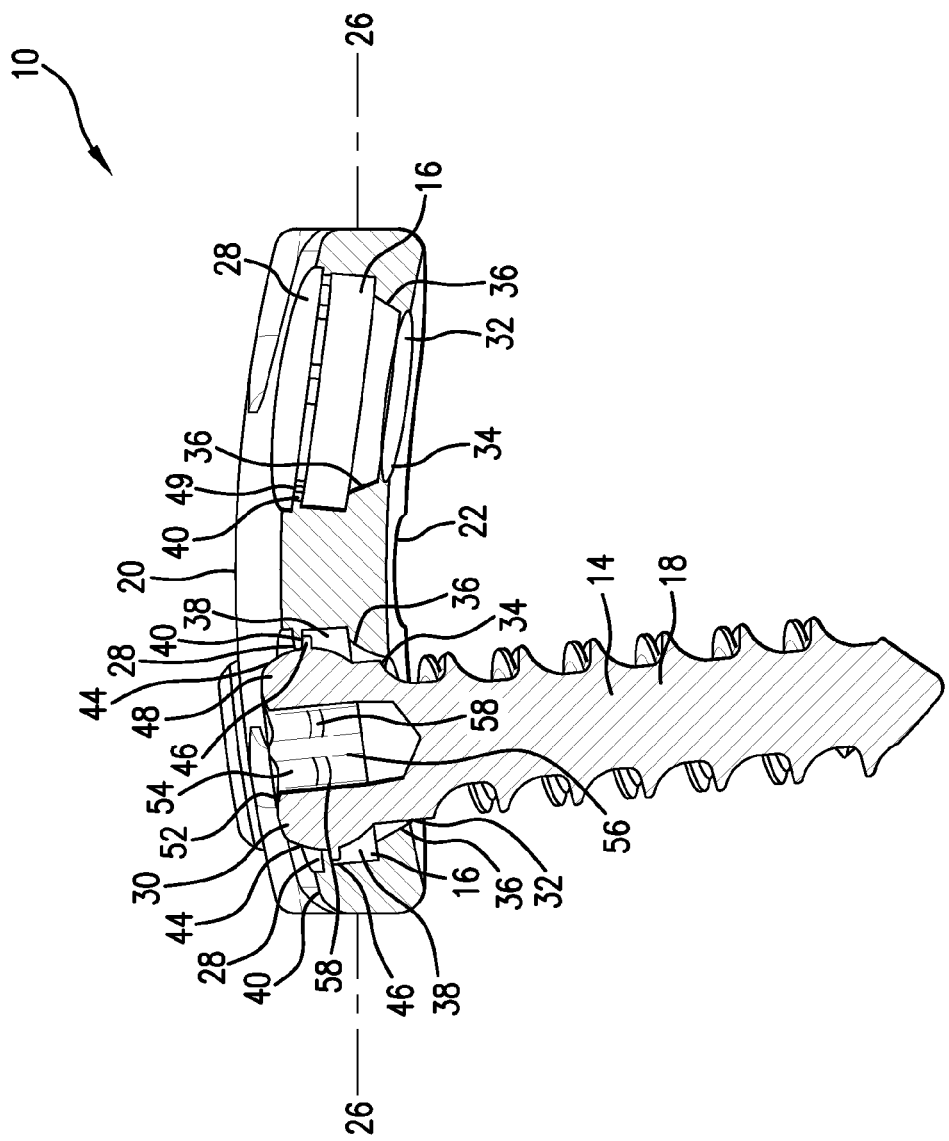
Figure 2B:
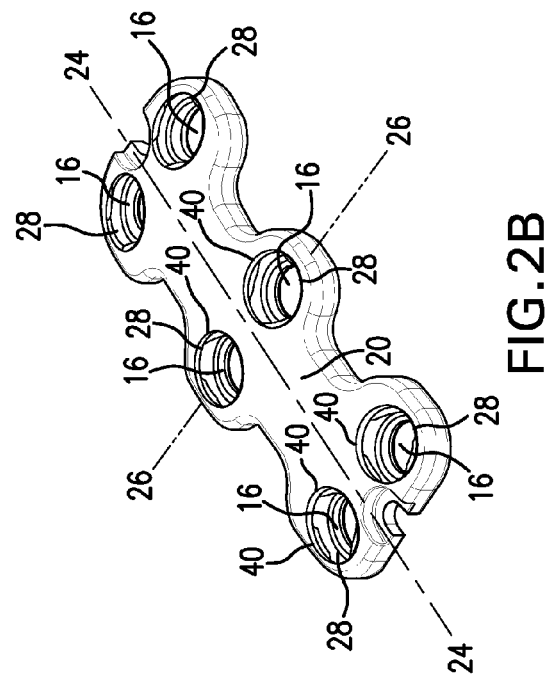
FIGS. 2A-D respectively show top, isometric, side and cross-sectional views of the low profile anterior vertebral plate.
Figure 2D:
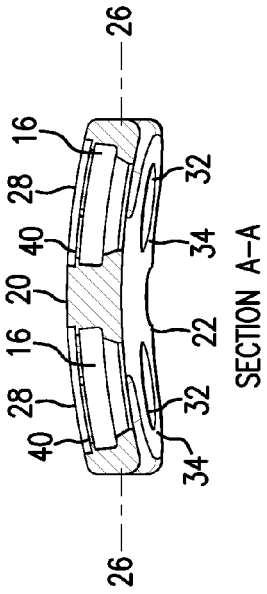
Figure 2A:
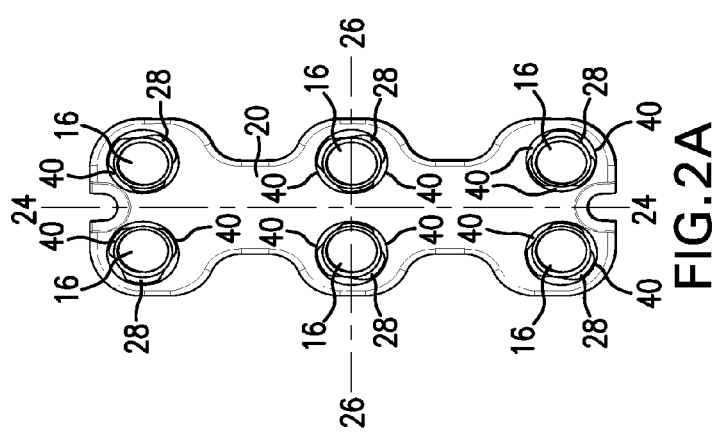
Figure 2C:
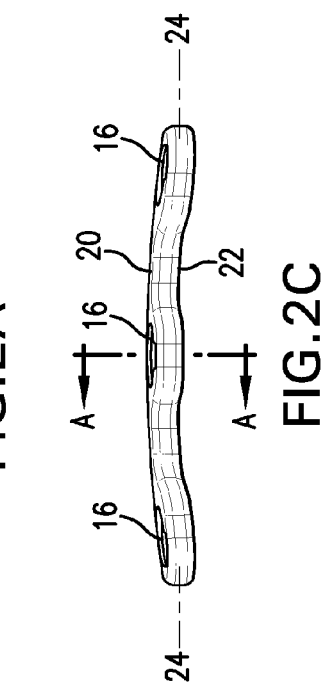
Figure 4B:
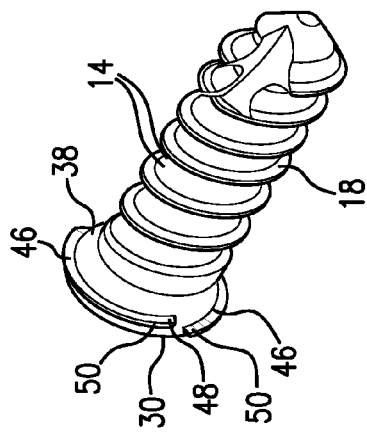
Figure 4D:
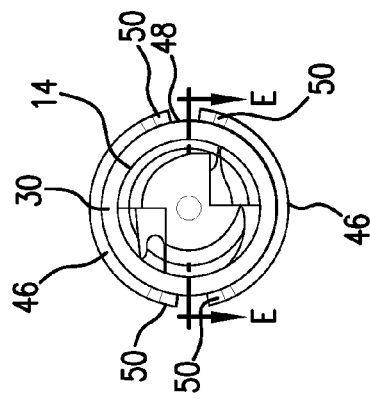
Figure 4A:
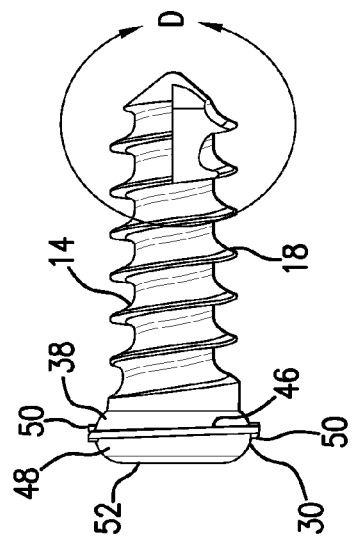
Figure 4C:
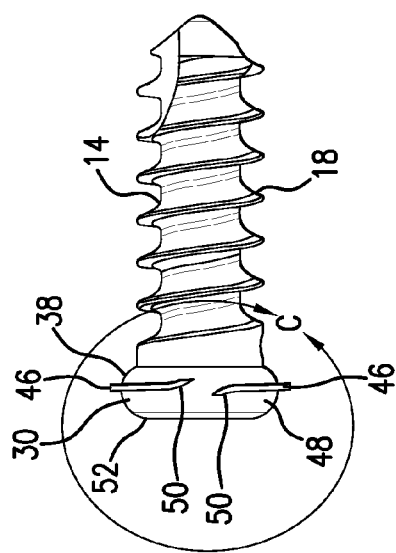

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

The system, as generally shown at 10 in FIGS. 1A-E, includes a low profile anterior vertebral body plate 12 that, when implanted in a patient, can be secured to the underlying bone using quick lock bone screws 14 as shown in FIGS. 1A-E, 3A-E, and 4A-G. The vertebral body plate 12, as shown in FIGS. 1A-E, and 2A-D can be provided as an elongated, low profile, plate structure that defines at least one and preferably multiple screw holes 16, which are sized and configured to permit through passage for the threaded portion 18 of the bone screw 14 from the plate upper surface 20 to the plate lower surface 22.

As shown in FIGS. 1A-E and 2A-D the plate 12 can be configured to be generally planar; however, the plate preferably will be formed to have arcuate upper and lower surfaces 20, 22, arcing along both the longitudinal axis 24 as well as the transverse axis 26 of the plate 12. This arcing of the plate surface provides a better conformational fit to the anterior surface of the vertebrae to which the plate is to be attached. Each of the screw holes 16, which are defined as through passages in the plate 12, is configured at the upper portion 28 to be generally circular and sized to circumferentially surround the screw head 30 when the screw 14 is fully seated in the plate 12. The lower portion 32 of the screw hole 16 is configured to have an inwardly projecting edge 34, which is formed by the generally inward slanting or rounded concave shaped surface 36 of the lower portion 32 of the plate wall defining the screw hole 16. This inward slating or rounded concave shaped surface 36 can have a complementary shape to that of the underside 38 of the screw head 30.

The inner most surface of the plate wall defining the upper portion 28 of the screw hole 16 can include at least one inwardly projecting flange 40, as shown in FIGS. 1A,B and E. The at least one inwardly projecting flange 40 forms a non-continuous circular shaped entry portal 42 for the screw hole 16 upper portion 28. Preferably, multiple inwardly projecting flanges 40 can be provided, each of the flanges 40 being in an approximate alignment with the other flanges 40. The edges terminal edges of each of the flanges can be provided with a taper 44.

As shown in FIGS. 3A-E and 4A-G the quick lock bone screw 14 includes at least one locking thread 46 extending radially from at least a portion of the screw head 30 side wall 48. The at least one locking thread 46 can have a virtually flat pitch that rapidly transitions at each end of the thread to form an angled flange engagement/release terminus 50. As best shown in the detail FIG. 3E, the engagement/release terminus 50 at each end of the locking thread 46 is provided with an angle suitable to facilitate contact and engagement with one of the inwardly projecting flanges 40 provided on of the inner wall of the screw hole 16 when the screw 16 is turned in a clockwise direction. The other end of each of the locking threads is provided with an angle suitable to facilitate release of the locking thread 46 from the flange 40 when the screw 16 is turned in a counterclockwise direction.

Upon insertion of an appropriate tightening/loosening tool and the application of clockwise directed torque, the bone screw 14 is drawn by the normal pitched threads of the threaded portion 18 of the screw 14 through the screw hole 16 and into the underlying bone material. When the screw head 30 is fully seated in the screw hole 16, the locking thread 46 contacts the screw hole flange 40 and due to the angled thread terminus 40 interacting with the taper 44 of the flange 40, the locking thread 46 is drawn beneath the flange 40 and into a locked position. Due to the initial contact of the locking thread 46 to the flange 40, an increased tactile indication of increase rotational resistance can be felt during the locking of the screw 16 to the plate 12. The resistance is quickly overcome as the locking thread 46 is drawn below the flange 40. Additional clockwise screw rotation continues to draw the screw into the bone and pulls the screw head 30 into a fully seated position in the screw hole 16 of the plate 12. The additional rotation and resulting further advancement of the screw 14 into the underlying bone serves to pull the screw head 30 against the lower portion of the screw hole 32 and thus forces the plate 12 securely against the surface of the underlying bone. A counter-clockwise rotation of the screw 14 can cause the upwardly angled terminus 50 of the locking thread 46 to engage the flange 40 and draw it into a position beneath the locking thread 46 thus releasing the screw head 30 from a locked position with the screw hole 16.

The thread engaging taper 44 of the flange 40 can provide a more accommodating surface edge by which the flange 40 and the locking thread 46 of the screw 14 can become threadably engaged and interact during insertion, removal, and locking of the screw 14 to the plate 12.

As best shown in FIGS. 1A,B,E and FIGS. 3D and 4F, the upper surface 52 of the screw head 30 can define a tool receiving recess 54, which is sized and configured to operationally engage a tightening/loosening/removal tool as needed. Tool gripping elements 56 can be defined on the inner surface of the tool receiving recess 54, the gripping elements 56 being of a complementary shape to the tool being used. Any of a variety of known or novel shapes for gripping elements 56 can be used so long as they are complimentary to the shape of the tool employed. As shown in the non-limiting exemplary embodiment of the bone screw 14 depicted in FIGS. 1E and 4F, the screw head 30 can be provided with at least one loosening/removing tool engaging surface 58, which can be defined in the tool receiving recess 54. This removing tool engaging surface 58 can be of any configuration and can be located within the tool receiving recess 54 or on any accessible surface of the screw head 30 so long as the engaging surface is configured and positioned to facilitate the screw head 30 being grasped and pulled in an upward direction away from the plate 12 during the simultaneous application of reverse torque to effect the screw 14 and plate 12 disengagement and removal process.

The use of a loosening/removing tool configured to engage the removing tool engaging surfaces 58 defined in the screw head 30 can facilitate the disengagement of the at least one locking thread 46 from the respective flange 40 in that the loosening/removing tool can engage the engaging surfaces 58 in the screw head 30 as the tool is simultaneously pulled away from the plate and turned in a counter-clockwise direction.

Further, the curvate underside 38 of the screw head 30 during screw insertion enables articulation of the screw head with the complimentary conformation of the lower portion 32 of the screw hole 16. This capacity for the screw head 30 to articulate during the screw insertion process and then be locked into position relative to the plate 12 enables the screw to be polyaxial in relationship to the plate as necessary. This polyaxial feature is a distinct advantage for a secure attachment to the underlying bone.

The above described method of use of the system 10 can be employed as a method of stabilizing or fixing injured or diseased vertebrae and if necessary, multiple devices or a device, which is elongated beyond the examples depicted herein, can be employed as necessary.

While the device as described herein can be preferably used to attach to the anterior surface of cervical vertebrae and is configured to be capable of stabilizing cervical vertebrae, it is within the inventors' understanding that the plate can be configured and adapted to conform to any implantable surgical plate requirement to provide a low profile plate capable of securing and stabilizing any injured or diseased bone.

The device 10 can be manufactured as integral components by methods known in the art, to include, for example, molding, casting, forming or extruding, and machining processes. The components can be manufactured using materials having sufficient strength, resiliency and biocompatibility as is well known in the art for such devices. By way of example only, suitable materials can include implant grade metallic materials, such as titanium, cobalt chromium alloys, stainless steel, or other suitable materials for this purpose. It is also conceivable that some components of the device can be made from plastics, composite materials, and the like.

It is also within the concept of the inventors to provide a kit, which includes at least one of the vertebral plate and quick lock screw systems disclosed herein. The kit can also include additional orthopedic devices and instruments; such as for example, instruments for tightening or loosening the bone screws, spinal rods, hooks or links and any additional instruments or tools associated therewith. Such a kit can be provided with sterile packaging to facilitate opening and immediate use in an operating room.

Each of the embodiments described above are provided for illustrative purposes only and it is within the concept of the present invention to include modifications and varying configurations without departing from the scope of the invention that is limited only by the claims included herewith.

What is claimed is:

1. A novel bone plate system, comprising:
    a plate having an upper surface and a lower surface, said plate defining at least two bone screw holes, said bone screw holes having a generally circular lower portion and an upper portion having at least one inwardly directed flange, said upper portion having a non-continuous circular configuration interrupted by said at least one inwardly directed flange,
    a least two quick lock screws corresponding to said at least two bone screw holes, said quick lock screws comprising an upper screw head and a lower threaded portion, said upper screw head having a first thread, which comprises at least one locking thread disposed along at least a portion of the side of the screw head, said lower threaded portion having a second thread, said second thread on said lower threaded portion being distinct from and non-continuous with said first thread of said upper screw head, said locking thread disposed on the side of the said screw head having a first end and a second end, a portion of said locking thread being perpendicular to a longitudinal axis of the screw head, the locking thread rapidly transitioning at the first and second ends to form an angled flange engagement/release terminus located on said upper screw head,
    wherein each of said quick lock screws is configured such that said engagement/release terminus of said locking thread bone screw insertion is capable of engaging and then passing beneath said at least one inwardly directed flange of said screw hole into a locked position and during bone screw removal is capable of disengaging from said at least one inwardly directed flange of said screw hole.

2. The bone plate system of claim 1, wherein bone screw is capable of polyaxial alignment with said plate.

3. The bone plate system of claim 1, wherein said plate is an anterior vertebral body plate.

4. The bone plate system of claim 1, wherein said bone screw and said locking thread are integrally formed.

5. The bone plate system of claim 1, wherein said plate is configured to have an upper and lower curved surface, said curve being along the longitudinal axis of the plate.

6. The boric plate system of claim 1, wherein said plate is configured to have an upper and lower curved surface, said curve being along the transverse axis of the plate.

7. The bone plate system of claim 5, wherein said curve is also along the transverse axis of the plate.

8. The bone plate system of claim 1, having a low profile such that no features of said device extend above the level of the upper surface of said plate.

9. The bone plate system of claim 1, wherein said bone screw head has a curvate underside of a complimentary configuration to said lower portion of said bone screw hole wherein said screw head and said lower portion of said bone screw hole are capable initially of rotational interaction such that bone screw when fully seated and locked into position within said plate is capable of being polyaxial relative to said plate.

10. A method of stabilizing a vertebral body, the method comprising,
    providing a bone plate system according to claim 1,
    surgically accessing an anterior surface of a vertebral body in need of stabilization,
    positioning said bone plate and attaching same to said vertebral body using quick lock screws.

11. A kit comprising at least one system according to claim 1 and at least one other tool or instrument for use in orthopedic surgery.

12. The bone plate system of claim 1, wherein upon the locking thread engaging the at least one inwardly directed flange, an increased tactile indication of rotational resistance is present, the rotational resistance being overcome as the locking thread is rotated and drawn below the at least one inwardly directed flange.

13. The bone plate system of claim 12, wherein additional rotation continues to draw the at least two lock screws into a fully seated position in the corresponding at least two bone screw holes.

* * * * *